United States Patent [19]

Jacobson

[11] 4,059,645

[45] Nov. 22, 1977

[54] ALKYLAROMATIC ISOMERIZATION PROCESS

[75] Inventor: Robert L. Jacobson, Pinole, Calif.

[73] Assignee: Chevron Research Company, San Francisco, Calif.

[21] Appl. No.: 740,580

[22] Filed: Nov. 10, 1976

[51] Int. Cl.$^2$ .............................................. C07C 5/24
[52] U.S. Cl. ............................ 260/668 A; 260/668 R; 208/139
[58] Field of Search ...................... 260/668 A, 668 R; 208/139

[56] References Cited

U.S. PATENT DOCUMENTS

| 3,078,318 | 2/1963 | Berger | 260/668 A |
|---|---|---|---|
| 3,381,048 | 4/1968 | Lovell et al. | 260/668 A |
| 3,415,737 | 12/1968 | Kluksdahl | 208/139 |
| 3,538,173 | 11/1970 | Berger et al. | 260/668 A |
| 3,553,276 | 1/1971 | Berger et al. | 260/668 A |
| 3,577,475 | 5/1971 | Csicsery | 260/668 A |
| 3,632,835 | 1/1972 | Mitsche et al. | 260/668 A |
| 3,879,484 | 4/1975 | Pollitzer | 260/668 A |
| 3,997,618 | 12/1976 | Cornely et al. | 260/668 A |

Primary Examiner—Veronica O'Keefe
Attorney, Agent, or Firm—D. A. Newell; R. H. Davies; W. D. Reese

[57] ABSTRACT

An alkylaromatic hydrocarbon is isomerized by contacting a feed including the alkylaromatic and hydrogen in the presence of 1.5–150 ppm free chloride, and not more than 10 ppm water, with a catalyst containing platinum, rhenium and more than 1.2 weight percent combined chloride on an alumina support at 650°–950° F and 100–300 psi hydrogen pressure.

5 Claims, No Drawings

ALKYLAROMATIC ISOMERIZATION PROCESS

BACKGROUND OF THE INVENTION

The present invention relates to a process for isomerizing alkylaromatic hydrocarbons.

It is often desirable to convert one alkylaromatic hydrocarbon to a more valuable isomer thereof. For example, it is often desired to convert ethylbenzene and metaxylene into paraxylene and/or orthoxylene. Processes for producing particular xylene isomers from $C_8$ alkylaromatic feedstocks are well known. Typically, a selected xylene isomer is recovered from a petroleum fraction, such as reformate, which is rich in $C_8$ alkylaromatics, by fractionation, crystallization or a molecular sieve-type separation operation. After the selected isomer has been removed from the fraction, the $C_8$ alkylaromatic residue is typically treated in a $C_8$ alkylaromatic isomerization operation in order to form additional amounts of the selected isomer. The newly formed amounts of the desired isomer are then recovered from the isomerate by the same type separation operation used with the original petroleum fraction. In converting the various $C_8$ alkylaromatic isomers, it has been found that ethylbenzene is relatively difficult to convert to xylene as compared to the relatively easy conversion of one xylen isomer to another. Prior art has acknowledged the difficulty of converting ethylbenzene, and the problem of ethylbenzene buildup in isomerization-separation systems has been an economic and technical drawback in many isomerization operations.

Various isomerization catalysts and flow schemes have been suggested by the art in attempting to provide efficient isomerization and isomer recovery systems for producing a selected $C_8$ alkylaromatic isomer. For example, U.S. Pat. No. 25,753 discloses a two-stage process for isomerizing xylenes. In the first stage, a xylene, or a nonequilibrium mixture of xylenes, is contacted with a hydrogenation-dehydrogenation catalyst under hydrogenation conditions to convert a large proportion (10–35%) of the xylenes in the feed to naphthenes. In the second stage, the naphthenes formed in the first stage are contacted with a hydrogenation-dehydrogenation catalyst under dehydrogenation conditions to reconvert the naphthenes to xylenes and simultaneously to isomerize the xylenes during the dehydrogenation. One catalyst described as useful in the process is platinum on alumina or silica-alumina.

U.S. Pat. No. 3,078,318 describes the isomerization of a xylene or nonequilibrium mixture of xylenes with a platinum-halogen-alumina catalyst in a hydrogen atmosphere at 700°–1100° F and 1–1500 atmospheres pressure. A selected xylene isomer is separated from the isomerization reactor effluent and the residue from the isomer-separation step is recycled to the isomerization step.

U.S. Pat. No. 3,381,048 describes a process for isomerization of a xylene isomer or a nonequilibrium mixture of xylene isomers using a platinum-halogen-alumina catalyst. In the process, the water content of the hydrocarbon feed to the isomerization reactor is kept at 20–200 ppm.

U.S. Pat. No. 3,538,173 describes a process for isomerizing xylenes in which ethylbenzene in a $C_8$ alkylaromatic-rich stream is isomerized to xylenes by controlling the $C_8$ napthenes content in the feed introduced into the isomerization reactor to keep the $C_8$ naphthenes content of the feed at 2–9 weight percent of the $C_8$ alkylaromatic content of the feed. A platinum-halogen-alumina catalyst is employed in the isomerization reactor at a temperature of 700°–840° F and a pressure of 3–20 atmospheres. U.S. Pat. No. 3,553,276 describes a process for isomerizing xylenes in which, during recovery of a selected xylene isomer from the isomerization reactor effluent, loss of $C_8$ naphthenes from the system is minimized by maintaining a high concentration of diluent toluene in the effluent from the isomerization reactor. The retention of $C_8$ naphthenes is accomplished by introducing large amounts of diluent toluene into the isomerization reactor in the feed. A platinum-halogen-alumina catalyst is used in the isomerization step at a temperature of 30°–1290° F and a pressure of 1–100 atmospheres, or more.

U.S. Pat. No. 3,879,484 describes a process for isomerizing $C_8$ alkylaromatic hydrocarbons, such as xylenes, by contacting the $C_8$ alkylaromatic hydrocarbons with a platinum-rhenium-halogen alumina catalyst at a temperature of 30°–1112° F and a pressure of 1–100 atmospheres; see also U.S. Pat. No. 3,577,475.

Activity and stability are important properties of an isomerization catalyst. One measure of activity is the capacity of a catalyst to provide sufficient conversion at any given operating temperature to achieve a close approach to equilibrium concentrations of isomers in the product. Stability refers to the ability of a catalyst to maintain a desired level of activity over an extended period of use without the need for excessively increasing the operating temperature. Typically, when a catalyst begins to lose activity, the operating temperature of the isomerization process is increased to maintain the desired activity level. A stable catalyst requires only a relatively slow temperature increase, while a relatively less stable catalyst requires a more rapid increase in temperature to maintain the same activity level.

In a $C_8$ alkylaromatics isomerization system for producing paraxylene and/or orthoxylene with a catalyst containing platinum and halogen, the temperature is typically raised at a constant rate, or stepwise, to maintain catalyst activity at a given level. It has been found necessary, when the temperature is thus raised, to likewise raise the hydrogen pressure in the isomerization system simultaneously to maintain an acceptable level of conversion of ethylbenzene to xylenes. An increase in hydrogen pressure in the isomerization system causes an increase in saturation of $C_8$ alkylaromatics in the feed to form $C_8$ naphthenes, i.e., the selectivity of the catalyst for isomerization is reduced by increasing the hydrogen pressure. The formation of excessive amounts of $C_8$ naphthenes is undesirable because it (1) consumes hydrogen and (2) consumes $C_8$ alkylaromatic hydrocarbons. This necessitates addition of undesirably large amounts of expensive hydrogen to the system and also reduces the potential $C_8$ alkylaromatic product isomer yield. Thus, it is apparent that the stability of an isomerization catalyst is important to economical operation of an isomerization system because it allows the system to operate at a lower temperature for a longer time, thereby providing greater overall catalyst selectivity.

In an embodiment, the present invention relates to an improved process for isomerizing an alkylaromatic hydrocarbon by contacting a feed including the hydrocarbon and hydrogen with a catalyst including 0.01–3 weight percent platinum and 0.01–3 weight percent rhenium on an alumina support at isomerization conditions including a temperature of 700° F to 900° F and a hydrogen pressure between 100 psi and 300 psi, the improvement comprising increasing the activity and selectivity of the catalyst by the method comprising: including in the catalyst greater than 1.2 weight percent combined chloride and contacting the feed with the catalyst in the presence of between 1.5 and 150 ppm, by volume, of free chloride and not more than 10 ppm, by volume of water, based on the volume of the feed.

I have found that a particularly effective process for isomerizing alkylaromatic hydrocarbons is obtained by employing particular isomerization conditions in combination with a particular isomerization catalyst. The feed is contacted with the catalyst in the presence of 1.5–150 ppm free chloride under very dry conditions, in the presence of not more than 10 ppm, and preferably below 1 ppm, water. The catalyst employed in the process of the invention is a platinum-rhenium-alumina composition which has a combined chloride content adjusted to above 1.2 weight percent and preferably about 1.5 weight percent. When the above-described isomerization conditions are used in conjunction with the high cloride platinum-rhenium catalyst, a particularly active, selective and stable isomerization system is achieved.

DETAILED DESCRIPTION OF THE INVENTION

The isomerizable alkylaromatic hydrocarbons which can be isomerized according to the present invention include orthoxylene, metaxylene, paraxylene, ethylbenzene, orthomethylethylbenzene, metamethylethylbenzene, paramethylethylbenzene, trimethylbenzenes, diethylbenzenes, propylbenzenes, methylpropylbenzenes, etc., and nonequilibrium mixtures thereof. The preferred isomerizable hydrocarbons are the $C_8$ alkylaromatics, i.e., the xylenes and ethylbenzene. Mixtures of $C_8$ alkylaromatics containing a less than equilibrium concentration of a desired $C_8$ aromatic isomer are also preferred. For example, a hydrocarbon mixture containing greater than equilibrium concentrations of ethylbenzene and metaxylene and less than equilibrium concentrations of orthoxylene and/or paraxylene is preferred for use. A source of the isomerizable hydrocarbon may be a petroleum fraction or refinery stream containing a high or low, but greater than equilibrium, concentration of the isomerizable hydrocarbon, such as a $C_8$ reformate fraction from which all or a part of a desired isomer has been removed. The isomerizable hydrocarbon may be employed diluted by hydrocarbons including aromatics, paraffins and naphthenes, etc.

The catalyst employed in the present process includes 0.01–3 weight percent platinum and 0.01–3 weight percent rhenium on an alumina carrier. The catalyst also includes at least 1.2 weight percent combined chloride. Combined chloride is chloride chemically bound to the catalyst, as by substitution for hydroxyl groups in the alumina carrier. The catalyst can be prepared by suitable known methods, such as by aqueous impregnation of particulate alumina with the platinum, rhenium and chloride, followed by drying and calcination. For example, an aqueous solution of chloroplatinic acid, perrhenic acid and hydrochloric acid may suitably be used for impregnation of an alumina carrier. The preferred alumina carrier is preferably prepared by treating an alpha-alumina monohydrate with a monobasic acid, neutralizing the acid with a nitrogen base, such as ammonia, shaping the resulting mass into the desired particle form, and then drying and calcining. The catalyst used in the process must contain at least 1.2 weight percent combined chloride, and preferably contains at least 1.5 weight percent combined chloride, based on the total weight of the catalyst. Preferably, the combined chloride component is added to the catalyst at the same time as the platinum component. The platinum and rhenium components each preferably make between 0.1 and 1 weight percent of the total catalyst weight.

The isomerization process may be carried out in any suitable, conventional reaction vessel or in a plurality of such reaction vessels connected in series or in parallel, and the process may be performed as a batch-type operation or a continuous-type operation. The catalyst may be used in a fixed bed or a moving bed system. A continuous-type operation using a fixed bed of the catalyst is preferably employed, with the feed being passed continuously through the catalyst bed.

Isomerization conditions employed in the process include a temperature between 700° F and 900° F, preferably between 750° F and 850° F. A hydrogen pressure of 100 psi to 300 psi is used, with a hydrogen pressure between 150 psi and 250 psi being preferred.

The feed which is contacted with the isomerization catalyst in the process includes the isomerizable hydrocarbons and hydrogen. The amount of hydrogen needed is sufficient to supply the required hydrogen pressure in the system and to provide a hydrogen-hydrocarbon of a ratio of from about 2 to about 20. The feed is preferably continuously passed in contact with the catalyst at a liquid hourly space velocity (LHSV) between 0.1 and 10, with a LHSV of about 0.5 to 3 being preferred.

The feed is contacted with the catalyst in the presence of free chloride in an amount between 1.5 ppm and 150 ppm, by volume, based on the volume of the feed, with the preferred free chloride concentration being between 5 ppm and 100 ppm, volume, calculated on the feed volume. Free chloride is all chloride not in chemical combination in the catalyst. Free chloride or a substance which forms free chloride may be added to the feed, when necessary, by any conventional means, such as in the form of molecular chloride or an organic chloride, e.g., carbon tetrachloride. Free chloride or a chloride-forming substance may also be added directly to an isomerization reactor.

In a preferred embodiment of the process, hydrogen is continuously recycled to form a part of the feed, after having been separated from the isomerized hydrocarbon product. In such an operation, the free chloride contained in the recycled hydrogen (primarily as hydrogen chloride) is at a fairly high concentration and may provide at least a portion of the 1.5–150 ppm free chloride concentration which is needed. Generally, recycled hydrogen can supply 65–85% of the total amount of free chloride required during isomerization. Thus, the total amount of free chloride which is added to the system continuously or intermittently may be small in relation to the total free chloride contacted with the isomerization catalyst, when recycled hydrogen is used.

According to the invention, the feed is contacted with the isomerization catalyst in the presence of not more than 10 ppm, by volume of water, based on the volume of the feed. The hydrocarbon charge used in the process preferably has a water content of less than 1 ppm (vol.). Normally, the supplies of isomerizable alkylaromatic hydrocarbons which can be obtained from readily accessable sources, such as petroleum refineries, contain a greater amount of water than is permissible in feeds which can be used in the present process. Accordingly, the hydrocarbons must normally be dried before use in the process to provide the dry conditions required. The alkylaromatic hydrocarbon may be dried by, for example, distillation drying, contact with a drying agent, such as a molecular sieve, or another conventional drying procedure, capable of removing sufficient water from the hydrocarbon. Hydrogen is preferably conserved in the isomerization system by separating it from hydrocarbon products and recycling it continuously to form part of the feed. Only a small amount of makeup hydrogen is normally needed in the process when such a recycle is practiced. In such cases, it may not be necessary to subject makeup hydrogen to a drying procedure, unless the make-up hydrogen contains more than 50 ppm, by volume, of water. Thus, in some embodiments only the hydrocarbon component of the isomerization feed need be dried, because the recycled hydrogen component of the feed is already sufficiently dried.

After carrying out the isomerization operation, the desired alkylaromatic isomer may be recovered in a conventional manner. In a $C_8$ alkylaromatic isomerization operation, the product isomer is usually paraxylene or orthoxylene. In the case of paraxylene recovery, hydrogen is normally first separated from the reactor effluent and recycled. Then, a $C_8$ fraction is formed and processed to recover the paraxylene, as by paraxylene crystallization or molecular sieve isomer separation in a manner known to those skilled in the art. In the case of orthoxylene recovery, hydrogen is also separated and recylcled in a preferred embodiment; however, orthoxylene has a boiling point sufficiently different from other $C_8$ alkylaromatic isomers to allow it to be separated from the other isomers by fractional distillation.

One preferred method for separating paraxylene is by fractional crystallization of paraxylene from a $C_8$ alkylaromatic fraction. Generally, the $C_8$ alkylaromatic fraction is cooled to a low temperature, e.g., $-100°$ F. The cooling of the fraction results in crystallization of part of the fraction, with the crystals being rich in paraxylene. The crystals are then separated from the paraxylene-lean mother liquor by, for example centrifugation. The paraxylene concentration of the crystals which are recovered can be increased by serial crystallization procedures, by the use of other solvents, and by other known methods. Further details of crystallization procedures which are suitable may be obtained from U.S. Pat. Nos. 2,985,694 and 3,467,724, the teachings of which are incorporated herein by specific reference.

The residue left after recovery of the desired alkylaromatic hydrocarbon isomer may be recycled to form a part of the feed which is contacted with the isomerization catalyst. Thus, the hydrocarbons which are in the feed preferably include partly fresh feed hydrocarbons and partly recycled hydrocarbons.

The following examples illustrate a preferred embodiment of the present invention.

EXAMPLE I

A hydrocarbon stream containing the alkylaromatic hydrocarbons shown in Table I was mixed with hydrogen containing sufficient hydrogen chloride to provide the HCl contents in the feeds as shown in Table I and processed in a pilot plant isomerization reactor in a series of runs using a catalyst containing 0.3 weight percent platinum, 0.3 weight percent rhenium and varying amounts of combined chloride, as shown in Table I, on an alumina carrier. The free chloride used in the system was that contained in the HCl in the feed as shown in Table I. The operating conditions and results of the isomerization runs are shown in Table I for each run. It can be seen from the data in Table I that the process of the present invention provides superior results in isomerizing alkylaromatic hydrocarbons.

TABLE I

| Run | 1 | 2 | 3 | 4 | 5 | 6 | 7 | 8 | 9 | 10 |
|---|---|---|---|---|---|---|---|---|---|---|
| Feed Hydrocarbons, wt. % | | | | | | | | | | |
| Toluene | 6.3 | 6.3 | 6.3 | 6.3 | 6.3 | 6.3 | 6.3 | 6.3 | 6.3 | 6.3 |
| Metaxylene | 53.4 | 53.4 | 53.4 | 53.4 | 53.4 | 53.4 | 53.4 | 53.4 | 53.4 | 53.4 |
| Orthoxylene | 6.4 | 6.4 | 6.4 | 6.4 | 6.4 | 6.4 | 6.4 | 6.4 | 6.4 | 6.4 |
| Ethylbenzene | 24 | 24 | 24 | 24 | 24 | 24 | 24 | 24 | 24 | 24 |
| Paraxylene | 9.8 | 9.8 | 9.8 | 9.8 | 9.8 | 9.8 | 9.8 | 9.8 | 9.8 | 9.8 |
| Conditions | | | | | | | | | | |
| Feed water, ppm (vol.) | <1 | <1 | <1 | <1 | <1 | <1 | <1 | <1 | <1 | <1 |
| HCl in Feed, ppm (vol.) | 14 | 14 | 24 | 25 | 25 | 21 | 27 | 13 | 11 | 23 |
| $H_2$/HC mol ratio | 6 | 6 | 6 | 6 | 6 | 6 | 6 | 6 | 6 | 6 |
| LHSV | 1 | 2 | 1 | 1 | 2 | 2 | 2 | 2 | 1 | 2 |
| Temp, ° F | 800 | 850 | 800 | 850 | 850 | 800 | 850 | 800 | 800 | 850 |
| $H_2$ Pressure | 200 | 300 | 200 | 200 | 200 | 200 | 300 | 200 | 200 | 200 |
| Catalyst est. combined Chloride, wt. % | 1.4 | 1.2 | 1.7 | 1.4 | 1.4 | 1.6 | 1.7 | 1.4 | 1.3 | 1.4 |
| Product, wt. % of feed | | | | | | | | | | |
| Paraxylene | 17.1 | 15.8 | 17.5 | 17.1 | 16.8 | 16.2 | 17.2 | 15.3 | 17.1 | 16.7 |
| Ethylbenzene | 12.1 | 14.7 | 11.6 | 12.9 | 17.0 | 15.8 | 12.3 | 16.9 | 13.1 | 12.1 |
| Xylene loss | −3.0 | −0.3 | −5.5 | −2.3 | −2.5 | −2.4 | −3.6 | −1.2 | −3.7 | −4.9 |
| $C_8$ ring loss (Mol %) | 9.0 | 8.7 | 8.9 | 12.0 | 6.8 | 5.7 | 10.0 | 6.0 | 7.8 | 8.9 |
| Paraxylene, % approach to equil.[1] | 100 | 100 | 100 | 100 | 100 | 98 | 100 | 94 | 100 | 100 |
| Ethylbenzene, % approach to equil. | 64 | 47 | 70 | 60 | 38 | 44 | 65 | 37 | 60 | 63 |

[1]Based on xylenes in feed.

EXAMPLE II

Another hydrocarbon stream containing the alkylaromatic hydrocarbons shown in Table II was mixed with hydrogen containing hydrogen chloride to provide free chloride and processed in the same pilot plant isomerization reactor employed in the runs described in Example I. Two runs were made at two different levels of free chloride in the feed. In Run 11, the hydrogen included 25 ppm (vol) of HCl, while in Run 12, the hydrogen included 60 ppm (vol) of HCl. A catalyst containing 0.3 weight percent platinum and 0.3 weight percent rhenium was used. The combined chloride content of the catalyst for each run is shown in Table II. The operating conditions and results of the runs are shown in Table II. The results shown in Table II demonstrate that the process of the invention provides a highly efficient alkylaromatics isomerization process.

TABLE II

| | Runs | 11 | 12 |
|---|---|---|---|
| Feed Hydrocarbons, wt. % | | | |
| Toluene | | 11.9 | 11.9 |
| Paraxylene | | 0 | 0 |
| Metaxylene | | 34.7 | 34.7 |
| Orthoxylene | | 17.3 | 17.3 |
| Ethylbenzene | | 34.0 | 34.0 |
| Conditions | | | |
| Feed Water, ppm (vol) | | #1 | #1 |
| ppm (vol) HCl in Hydrogen | | 25 | 60 |
| H$_2$/HC mole ratio | | 6.1 | 6.0 |
| LHSV | | 2 | 2 |
| Temp., °F | | 792 | 792 |
| H$_2$ pressure | | 202 | 204 |
| Catalyst est. combined chloride, wt % | | 1.75 | 1.95 |
| Product, wt % of feed | | | |
| Paraxylene | | 18.7 | 22.4 |
| Ethylbenzene | | 18.5 | 15.9 |
| Xylene loss | | −18.7 | −22.4 |
| C$_8$ ring loss, % | | 4.4 | 5.5 |
| Paraxylene, % approach to equil. | | 92.3 | 97.3 |
| Ethylbenzene, mole % approach to equil. | | 58 | 68 |

What is claimed is:

1. In a process for isomerizing an alkylaromatic hydrocarbon by contacting a feed including said hydrocarbon and hydrogen with a catalyst including 0.01-3 weight percent platinum and 0.01-3 weight percent rhenium on an alumina support at isomerization conditions including a temperature of 700° F to 900° F and a hydrogen pressure between 100 psi and 300 psi, the improved method for increasing the activity and selectivity of said catalyst in said process comprising: including in said catalyst greater than 1.2 weight percent combined chloride and contacting said feed with said catalyst in the presence of between 1.5 and 150 ppm, by volume, of free chloride and not more than 10 ppm, by volume, of water, based on the volume of said feed.

2. A process according to claim 1 wherein said feed is contacted with said catalyst in the presence of not more than 1 ppm, by volume, water.

3. A process according to claim 1 wherein said hydrocarbon is selected from metaxylene and ethylbenzene.

4. A process according to claim 1 wherein said catalyst includes greater than 1.5 weight percent combined chloride.

5. A process according to claim 1 wherein said feed is contacted with said catalyst in the presence of 5-100 ppm, by volume, free chloride.

* * * * *

UNITED STATES PATENT AND TRADEMARK OFFICE
CERTIFICATE OF CORRECTION

PATENT NO. : 4,059,645
DATED : November 22, 1977
INVENTOR(S) : Robert L. Jacobson It is certified that error appears in the above-identified patent and that said Letters Patent are hereby corrected as shown below:

Col. 1, line 27, "xylen" should read --xylene--.

Col. 1, lines 35-36, "example, U.S. Pat. No. 25,753" should read --example, Reissue 25,753--.

Col. 2, line 61, insert heading --SUMMARY OF THE INVENTION--.

Col. 3, lines 18-19, "preferably about" should read --preferably above--.

Col. 4, lines 27-28, "hydrogen-hydrocarbon" should read --hydrogen/hydrocarbon--.

Signed and Sealed this

Eleventh Day of April 1978

[SEAL]

Attest:

RUTH C. MASON
Attesting Officer

LUTRELLE F. PARKER
Acting Commissioner of Patents and Trademarks